(12) United States Patent
Laurencin et al.

(10) Patent No.: US 8,945,218 B2
(45) Date of Patent: Feb. 3, 2015

(54) LIGAMENT AND TENDON REPLACEMENT CONSTRUCTS AND METHODS FOR PRODUCTION AND USE THEREOF

(75) Inventors: Cato T. Laurencin, Elkins Park, PA (US); Frank K. Ko, Philadelphia, PA (US); James A. Cooper, Philadelphia, PA (US); Helen H. Lu, New York, NY (US); Mohammed A. Attawia, Canton, MA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 11/753,889

(22) Filed: May 25, 2007

(65) Prior Publication Data
US 2007/0233242 A1    Oct. 4, 2007

Related U.S. Application Data

(63) Continuation of application No. 09/878,641, filed on Jun. 11, 2001, now abandoned, which is a continuation-in-part of application No. 09/814,427, filed on Mar. 22, 2001, now abandoned.

(60) Provisional application No. 60/191,999, filed on Mar. 24, 2000.

(51) Int. Cl.
| | |
|---|---|
| *A61F 2/02* | (2006.01) |
| *A61F 2/44* | (2006.01) |
| *A61F 2/08* | (2006.01) |
| *A61F 2/40* | (2006.01) |
| *A61F 2/38* | (2006.01) |

(52) U.S. Cl.
CPC ... *A61F 2/08* (2013.01); *A61F 2/40* (2013.01); *A61F 2/38* (2013.01); *A61F 2210/0004* (2013.01)
USPC ............... 623/13.17; 623/13.19; 623/13.2; 623/13.11; 623/13.18

(58) Field of Classification Search
USPC ............. 623/13.11, 13.12, 13.14, 13.19, 13.2
See application file for complete search history.

(56) References Cited

U.S. PATENT DOCUMENTS

| | | | | |
|---|---|---|---|---|
| 4,187,558 | A * | 2/1980 | Dahlen et al. | 623/13.14 |
| 4,728,329 | A * | 3/1988 | Mansat | 623/13.19 |
| 4,792,336 | A | 12/1988 | Hlavacek et al. | 623/13 |
| 4,917,699 | A | 4/1990 | Chervitz | 623/13.19 |
| 4,917,700 | A * | 4/1990 | Aikins | 623/13.19 |

(Continued)

FOREIGN PATENT DOCUMENTS

| | | |
|---|---|---|
| AU | 2001249322 | 10/2001 |
| CA | 2403983 | 10/2001 |

(Continued)

OTHER PUBLICATIONS

Bellincampi et al., "Viability of Fibroblast-Seeded Ligament Analogs after Autogenous Implantation", *Journal of Orthopaedic Research* 1998 16:414-420.

(Continued)

*Primary Examiner* — David Isabella
(74) *Attorney, Agent, or Firm* — Baker & Hostetler LLP

(57) ABSTRACT

Degradable, polymeric fiber-based, three-dimensional braided scaffolds for use as graft materials in ligament and tendon repair, reconstruction and replacement are provided. Also provided are methods for preparing these scaffolds.

18 Claims, 1 Drawing Sheet

(56) References Cited

U.S. PATENT DOCUMENTS

| | | | |
|---|---|---|---|
| 5,078,744 A | | 1/1992 | Chvapil |
| 5,217,495 A | * | 6/1993 | Kaplan et al. ............. 623/13.18 |
| 5,263,984 A | * | 11/1993 | Li et al. ..................... 623/13.18 |
| 5,376,118 A | | 12/1994 | Kaplan et al. .................. 623/11 |
| 5,383,925 A | | 1/1995 | Schmitt |
| 5,595,621 A | | 1/1997 | Light et al. |
| 5,711,960 A | | 1/1998 | Shikinami |
| 5,718,012 A | | 2/1998 | Cavallaro |
| 5,800,543 A | * | 9/1998 | McLeod et al. ............. 623/13.2 |
| 5,855,610 A | | 1/1999 | Vacanti et al. ............... 623/2.13 |
| 5,980,564 A | * | 11/1999 | Stinson ........................ 623/23.7 |
| 6,077,989 A | * | 6/2000 | Kandel et al. .............. 623/13.17 |
| 6,365,149 B2 | | 4/2002 | Vyakarnam et al. ......... 424/93.1 |
| 6,458,148 B1 | | 10/2002 | Dauner et al. ................ 606/228 |
| 6,866,681 B2 | | 3/2005 | Laboureau et al. |
| 2002/0133229 A1 | | 9/2002 | Laurencin et al. |

FOREIGN PATENT DOCUMENTS

| | | | |
|---|---|---|---|
| EP | 0 306 018 A1 | 3/1989 | |
| EP | 1272127 | 1/2003 | |
| JP | 07-148243 A | 6/1995 | |
| JP | H07-506995 | 8/1995 | |
| JP | H09-500298 | 1/1997 | |
| JP | 11-506611 T | 6/1999 | |
| JP | 4452426 | 10/2003 | |
| WO | WO 95/01810 | 1/1995 | |
| WO | WO 95/08354 A1 | 3/1995 | |
| WO | WO 95/25550 | 9/1995 | |
| WO | WO 96/40175 A1 | 12/1996 | |
| WO | WO 97/45147 | 12/1997 | |
| WO | WO 9745147 A1 * | 12/1997 | ............. A61L 27/00 |
| WO | WO 98/25637 A1 | 6/1998 | |
| WO | WO 01/72241 | 10/2001 | |

OTHER PUBLICATIONS

Friedman et al., "Autogeneic Anterior Cruciate Ligament (ACL) Anterior Reconstruction of the Knee", *Clinical Orthopaedics and Related Research* 1985 196:9-14.

Gazdag et al., "Alternatives to Autogenous Bone Graft: Efficacy and Indications", *J. Amer. Acad. Orthop. Surg.* 1995 3:1-8.

Goulet et al. "Tendons and Ligaments" In R.P. Lanza, R. Langer, and W.L. Chick (eds), Principles of Tissue Engineering, R.G. Landes Company and Academic Press, Inc. 1997 pp. 633-644.

Jackson et al., "Intraarticular reaction associated with the use of freeze-dried, ethylene oxide-sterilized bone-patella tendon-bone allografts in the reconstruction of the anterior cruciate ligament", *Amer. J. Sports Med.* 1990 18:1-11.

Jackson et al., "Biologic and Synthetic Implants to Replace the Anterior Cruciate Ligament", *Arthroscopy* 1994 10:442.

Jarcho M., "Calcium Phosphate Ceramics as Hard Tissue Prosthetics", *Clin. Ortho.* 1981 157:259-278.

Ko F.K. in Textile Structural Composites, eds. Chou T.W. and Ko F.K. Elsevier, Amsterdam 1989.

Langer et al., "Tissue Engineering", *Science* 1993 260:920-926.

Lin, et al., "Ligament Tissue Engineering using Synthetic Biodegradable Fiber Scaffolds", Tissue Engineering, 1999, vol. 5, No. 5, p. 443-452.

International Patent Application No. PCT/US2001/09079: International Search Report dated Aug. 2, 2001, 1 page.

\* cited by examiner

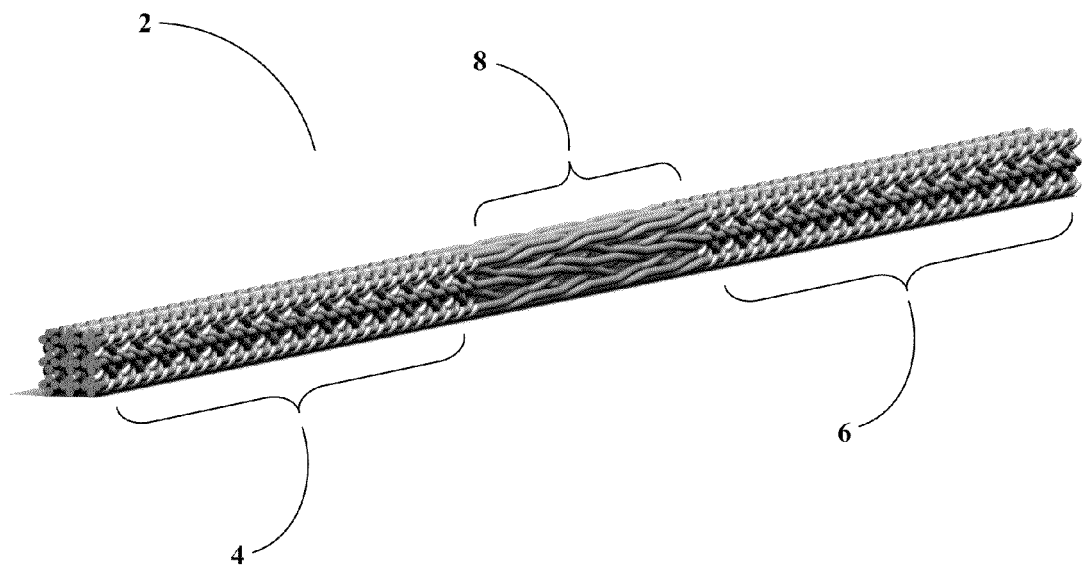

LIGAMENT AND TENDON REPLACEMENT CONSTRUCTS AND METHODS FOR PRODUCTION AND USE THEREOF

This patent application is a continuation of U.S. Ser. No. 09/878,641 filed Jun. 11, 2001 now abandoned, which is a continuation-in-part U.S. patent application Ser. No. 09/814,427, filed Mar. 22, 2001 now abandoned, which claims the benefit of priority from U.S. Provisional Application Ser. No. 60/191,999, filed Mar. 24, 2000, teachings of each of which are hereby incorporated by reference in their entirety.

This invention was supported in part by funds from the U.S. government (NIH Grant Nos. 5 F31 GM18905-02 and AR46117 and NSF Presidential Grant BES9553162/BES981782) and the U.S. government may therefore have certain rights in the invention.

FIELD OF THE INVENTION

The present invention relates to use of fiber technologies to design useful matrices for tissue engineering. In particular, a viable replacement construct of human ligaments and tendon is provided. This replacement construct comprises a degradable, polymeric fiber-based, three-dimensional braided scaffold. In one embodiment, the replacement construct is seeded with cells, preferably cells of mesenchymal origin or stem cells capable of generating mesenchymal cells. The biocompatability of this replacement construct coupled with the tissue engineering based design is expected to promote healing and repair of the damaged ligament or tendon.

BACKGROUND OF THE INVENTION

In orthopaedic reconstruction, surgeons often replace damaged tissue resulting from trauma, pathological degeneration, or congenital deformity with autogenous grafts (Langer, R. and Vacanti, J. P. *Science.* 1993 260:920). Reconstructive surgery is based upon the principle of replacing these types of defective tissues with viable, functioning alternatives. The grafting of bone in skeletal reconstruction has become a common task of the orthopaedic surgeon with over 863,200 grafting procedures performed each year in the U.S. For cartilage replacement, there are over 1,000,000 procedures of various types performed each year and for ligament repairs, there are approximately 90,000 procedures performed per year (Langer, R. and Vacanti, J. P. *Science.* 1993 260:920). Currently, autografts (Friedman et al. *Clin. Ortho.* 1985 196:9; Jackson et al. *Amer. J. Sports Med.* 1990 18:1) (tissue taken from the patient) and allografts (Gadzag et al. *J. Amer. Acad Ortho. Surg.* 1995 3:1; Shinoet al. *J. Bone and Joint Surg.* 1988 7011:556; Jackson et al. *Arthroscopy* 1994 10:442) (tissue taken from a cadaver) are the most common replacement sources for the treatment of musculoskeletal problems. In repair of ligament injuries, such as injury of the anterior cruciate ligament (ACL), a segment of the patellar tendon has been frequently used (Jackson et al. *Amer. J. Sports Med.* 1990 18:1). For cartilage and bone repair, transplantation of autogenous grafts has been the current treatment of choice.

However, there are various problems associated with these treatments. For example, for autogenous tissue, key limitations are donor site morbidity where the remaining tissue at the harvest site is damaged by removal of the graft, and the limited amount of tissue available for harvesting. The use of allografts attempts to alleviate these problems. However, this type of graft is often rejected by the host body due to an immune response to the tissue. Allografts are also capable of transmitting disease. Although a thorough screening process eliminates most of the disease carrying tissue, this method is not 100% effective.

As a result of the limitations with conventional reconstructive graft materials, surgeons have looked to synthetic alternatives.

Synthetic ligament grafts or graft supports include carbon fibers, Leeds-Keio ligament (polyethylene terephthalate), the Gore Tex prosthesis (polytetrafluoroethylene), the Stryker-Dacron ligament prosthesis made of Dacron tapes wrapped in a Dacron sleeve and the Gore-Tex ligament augmentation device (LAD) made from polypropylene. These grafts have exhibited good short term results but have encountered clinical difficulties in long term studies. Limitations of these synthetic ligament grafts include stretching of the replacement material, weakened mechanical strength compared to the original structure and fragmentation of the replacement material due to wear.

The ideal ligament or tendon replacement is biodegradable, porous, biocompatible, exhibits sufficient mechanical strength and promotes formation of ligament or tendon tissue.

Various researchers have disclosed potential ligament constructs comprising collagen fibers, biodegradable polymers and composites thereof. For example, collagen scaffolds for ACL reconstruction seeded with fibroblasts from ACL and skin have been described (Dunn et al. The Tissue Engineering Approach to Ligament Reconstruction. Material Research Society Symposium Proceedings 331, 13-18, 1994, Boston, Materials Research Society; Bellincampi et al. *J. Orthop. Res.* 1998 16:414-420). WO 95/2550 also discloses a prosthetic device for ligament repair comprising an arrangement of collagen threads.

A bioengineered ligament model, which differs from other ligament models in the addition of ACL fibroblasts to the structure, the absence of cross-linking agents and the use of bone plugs to anchor the bioengineered tissue, has also been described (Goulet et al. Tendons and Ligaments. In R. P. Lanza, R. Langer, and W. L. Chick (eds), Principles of Tissue Engineering, pp. 639-645, R. G. Landes Company and Academic Press, Inc. 1997).

U.S. Pat. No. 4,792,336 discloses a device with an absorbable component comprising a glycolic or lactic acid ester linkage. The device comprises a plurality of fibers comprising the absorbable component which can be used as a flat braid in the repair of a ligament or tendon.

The present invention relates to a graft material for use in ligament and tendon repair and reconstruction composed of a degradable, polymeric, fiber-based, three dimensional braided scaffold.

BRIEF DESCRIPTION OF THE DRAWINGS

The foregoing and other aspects of the present inventions will become apparent from the following detailed description when considered in conjunction with the accompanying drawings. For the purpose of illustrating the invention, there is shown in the drawings embodiments that are presently preferred, it being understood, however, that the invention is not limited to the specific aspects disclosed. The drawings are not necessarily drawn to scale.

In the drawings:

FIG. 1 depicts an exemplary three dimensional braid according to the present disclosure having first and second attachment ends and a middle region.

SUMMARY OF THE INVENTION

An object of the present invention is to provide a replacement construct comprising a degradable, polymeric, fiber-based, three-dimensional braided scaffold.

Another object of the present invention is to provide a replacement construct comprising a degradable, polymeric, fiber-based, three-dimensional braided scaffold which has been seeded with cells, the ingrowth of which is supported by the scaffold.

Another object of the present invention is to provide a method for repairing a damaged ligament or tendon in a human which comprises implanting at the damaged area a degradable, polymeric, fiber-based, three-dimensional braided scaffold.

Another object of the present invention is to provide a method for repairing a damaged ligament or tendon in a human which comprises implanting at the damaged area a degradable, polymeric, fiber-based, three-dimensional braided scaffold which has been seeded with cells, the ingrowth of which is supported by the scaffold.

Yet another object of the present invention is to provide a method for producing a graft material composed of living cells in a degradable matrix for use in ligament repair and reconstruction which comprises harvesting, growing and passaging cells in tissue culture and seeding the cultured cells onto a degradable, polymeric, fiber-based, three-dimensional braided scaffold.

DETAILED DESCRIPTION OF THE INVENTION

The present invention relates to an approach to tissue repair based upon the principle of using bioresorbable scaffolds to serve as templates for tissue regeneration. In particular, the present invention relates to degradable scaffolds, preferably polymeric, fiber-based three-dimensional (3-D) braided scaffolds based on hierarchical design methodology.

Fiber-based braided scaffolds of the present invention were compared with microfiber nonwoven matrices for tissue replacement applications.

An electrospinning technique was used to fabricate microfiber nonwoven matrices. The basis of this technique is the generation of an electric field between an oppositely charged polymer fluid and a collection screen. A polymer solution is added to a glass syringe with a capillary tip. An electrode is placed in the solution with another connection made to a copper screen. As the power is increased, the polymer solution becomes charged and is attracted to the screen. Once the voltage reaches a critical value, the charge overcomes the surface tension of the droplet and a jet of microfibers is produced. As the charged fibers are splayed, the solvent quickly evaporates and the fibers randomly accumulate on the surface of the collection screen. This results in a nonwoven mesh of micron scaled fibers. Fiber diameter and mesh thickness can be controlled by a number of different parameters including solution viscosity, voltage, distance between screen and tip, and duration of electrospinning.

The 3-D braided scaffolds of the present invention were formed using a 3-D textile braiding technique. An exemplary 3-D textile braiding technique is the 4-step process which uses a track and column method to create the fiber matrix. However, as will be understood by those of skill in the art upon reading this disclosure, other techniques for preparing 3-D braided scaffolds can also be used.

The 4-step braiding equipment consists of slotted tracks where bobbins and yarn carriers are located. Movement of the bobbins and carriers within the tracks is used to create vertical columns in the 3-D structure. Alternating rows and columns of the carriers in the braiding lattice are shifted to create the 3-D braid. The geometric parameters which determine the shape and fiber architecture of B 3-D braids includes braiding angle distribution, yarn volume fraction, number of carriers, and braiding yarn width. This highly versatile system allows for the formation of a variety of 3-D braided structures with different architecture and mechanical properties.

Based on these fiber and textile technologies, a microfiber nonwoven mesh and two rectangular 3-D braids were fabricated for cell culture experiments.

In these experiments, the response of cells to the hierarchical structure of the two fiber based matrices was compared. In particular, the ability of these matrices to serve as cellular scaffolds was evaluated using osteoblasts and fibroblasts in an in vitro environment.

Electron microscopy of the three matrix structures was first performed. Low magnification images showed basic matrix structure and organization. SEM analysis of the microfiber matrix showed a highly porous, fibrous structure resulting from the random arrangement of the fibers. PLAGA [50:50] fibers ranged in diameter from approximately 2-7 $\mu$m. Images of the 3-D braided matrices showed a highly organized fibrous structure resulting from the 3-D braiding process. The difference in the number of fibers/yarn was clearly evident in these two structures. Braid #1 which was fabricated from 30 yarn having 30 fibers/yarn had more individual braids throughout the structure than the Braid #2 matrix fabricated from 60 yarn with 60 fibers/yarn. These structures can be attributed to the packing density of the fibers. With half as many fibers per yarn, the 30 yarn of Braid #1 was able to pack into a tighter structure with a braid unit cell smaller than the 60 yarn matrix. SEM evaluation of these structures indicated that all matrices possessed the structural characteristics needed to function as a cellular scaffold.

However, the results of the in vitro study revealed that the cellular response was dependent on matrix structure. Both fibroblasts and osteoblasts had the same morphology on the microfiber nonwoven matrix. After one day of culture on the microfiber matrix, cells appeared spindle shaped and exhibited spreading over the surface. Slight cytoplasmic projections were seen extending from the body of the cells to the surface of the matrices. However, SEM did not reveal a microfiber structure in any of the samples, regardless of time point. Since only 50,000 cells were plated on a 1 cm$^2$ matrix, it is believed that the cells had completely spread over the surface obscuring the microfiber structure. The spindle shaped morphology observed at day 1 is indicative of initial attachment and not the formation of a cellular monolayer.

A degradation study was also performed to evaluate any changes to matrix structure due to degradation in the tissue culture media. This study revealed that the matrix quickly degraded while in the cell culture media. It is believed that exposure to DMEM caused the swelling and aggregation of the microfibers. Swelling was so significant in some samples that the structure lost almost all of its porosity. Thus, this degradation changed the matrix from a porous microfiber matrix to a non-porous mass of polymer during the course of the cell culture study.

Unlike the microfiber matrix, cell morphology on the 3-D braid differed between osteoblasts and fibroblasts. Over the course of the 2 week experiment, both cell types followed the characteristic sequence of events describing cell attachment, spreading and proliferation. However, the rate at which these events occurred differed for osteoblasts and fibroblasts. Further, cellular attachment appeared to be more pronounced with osteoblasts than fibroblasts. For example, at one day of cell culture on 3-D Braid #1, the osteoblasts showed significant spreading over the surface and the formation of a cellular layer. In comparison, the day 1 fibroblasts still retained a spindle shaped morphology characteristic of initial attachment. In addition, the fibroblasts had organized along the length of the fibers. The cells appeared to have grouped together along the groove created by two adjacent fibers. Slight cytoplasmic extensions were seen between the aligned cells.

Thus, as demonstrated by the cellular response observed in these experiments, hierarchical structure plays an important role in cellular morphology and organization. Cells responded dynamically to the changing structure of the quickly degrading matrix comprising the nonwoven microfiber. The cells did not organize on such a structure and morphology of the specific cell types was similar. In contrast, in the slowly degrading fiber structure of the 3-D braid, fibroblasts organized along the length of the fibers, and osteoblasts showed a distinctly different morphology than fibroblasts.

Accordingly, use of fiber technology in tissue engineering holds several advantages over a number of non-fibrous 3-D structures. Importantly, the ability to impart high levels of structural organization to the matrix allows for precise control of matrix structure. The 3-D braided and nonwoven matrices are exemplary of the range of 3-D fiber architectures that can be designed and produced. The braided matrix consisted of highly organized PLAGA yarns woven into a 3-D structure. Although the nonwoven matrix was the result of randomly oriented microfibers, the structure was highly uniform. Thus, both the 4-step 3-D braiding technique and the electrospinning process are useful fabrication methods showing high levels of versatility for various tissue engineering application. The ability to manufacture a variety of different matrices and to maintain precise control over matrix fabrication are extremely important factors in the design of a tissue engineered scaffold.

For example, the human knee contains large ligaments such as the ACL which connects the femur to the tibia and participates in motion control, acting as a stabilizer of joint movement. ACL is the most commonly replaced ligament of the knee, with over 250,000 patients each year diagnosed with ACL injury. This type of injury often occurs during sports and physical exercise, and frequently results in disabilities that can be permanent and disabling to the patient. Other exemplary ligaments which are oftentimes injured and require repair and/or replacement include, but are not limited to, the medical collateral ligament, the anterior talo-fibular ligament of the ankle and the glenohumeral ligaments. Exemplary tendons which are oftentimes injured and require repair and/or replacement include, but are not limited to, the patellar, the Achilles tendon and the rotator cuff.

It is believed that the 3-D braided scaffolds will be particularly useful as replacement constructs for the above-described exemplary ligaments and tendons, as well as any other ligaments or tendons which have been damaged, as these scaffolds are degradable, porous, biocompatible, exhibit sufficient strength and promote formation of ligament and tendon tissue. The fiber based design of the scaffold emulates the natural ligament or tendon and the braided structure offers mechanical strength as well as needed porosity for cell attachment and ingrowth.

While PLAGA fibers were used in the braided scaffold in the experiments described herein, as will be understood by those of skill in the art upon reading this disclosure, any and all biodegradable polymers can be used. Preferred biodegradable polymers are those degraded by hydrolysis. Examples of polymeric fibers useful in the present invention include, but are not limited to, fibers comprised of poly(hydroxy)esters, such as polylactic acid, polyglycolic acid and co-polymers thereof. Preferred biodegradable polymers are lactic acid polymers such as poly(L-lactic acid (PLLA), poly(DL-lactic acid (PLA), and poly(DL-lactic-co-glycolic acid) (PLGA).

The co-monomer (lactide-glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50 can also be used for these scaffolds. Other exemplary biodegradable polymers useful in the scaffolds of the present invention include, but are not limited to, polyorthoesters, polyanhydrides, polyphosphazenes, polycaprolactones, polyhydroxybutyrates, degradable polyurethanes, polyanhydrideco-imides, polypropylene fumarates, and polydiaxonane.

To aid in selection of polymer fibers to be used for the braiding of 3-D constructs for ligament and/or tendon replacement, the degradation characteristics of three types of polymer fiber bundles and the effect of degradation on long-term mechanical properties of these polymers was examined. The three polymers examined were multifilament fibers of L-poly-lactide (PLA, 70 denier), poly-glycolide (PGA, 60 denier) and their 82:18 co-polymer (PLAGA, 70 denier) laced into 10 multi-fiber bundles. The mass retention and mechanical properties of all the polymers decreased with increasing immersion time in both phosphate buffered saline (PBS) and cell culture medium ($\alpha$MEM). However, PGA bundles exhibited the most rapid loss of strength, mass and yarn integrity, and this polymer had largely degraded after 2 weeks and broken up into small fibers. PLA and PLAGA bundles degraded more slowly as reflected in decreases in their mechanical strength, mass retention and molecular weight. After 4 weeks, PLA sustained higher maximum tensile load than PLAGA. It was found that polymer mass retention was independent of changes in mechanical strength and molecular weight.

PLAGA molecular weight decreased to half of its original value after 2 weeks of immersion in $\alpha$MEM, which may be too fast for ligament healing to take place. As the polymers degraded, the pH of PBS decreased as acidic degradation products were released. While an initial decrease in pH was measured in $\alpha$MEM, the solution later returned to control values. This is likely due to protein adsorption and the higher buffering potential of $\alpha$MEM, rendering it a more realistic solution in which to model polymer degradation in vivo.

Thus, based on examination of changes in molecular weight, mechanical strength and mass retention as the polymer degraded, PLA (in comparison to PLAGA 82:18 or PGA) has specific advantages for use in the braided, tissue-engineered 3-D ACL replacement constructs of the present invention. Due to its accelerated degradation and loss of mechanical properties, PGA may be less preferred for ACL replacement.

Mechanical testing can be used to characterize the 3-D fibrous construct's stress-strain relationship. It is believed that similar stress-strain relationships to the rabbit ACL can be engineered with a hierarchical design using 3-D braiding of a fiber based absorbable scaffold. Accordingly, a structure to model a rabbit ligament can be created. This synthetic ligament should have a total gauge length of 1 cm. Mechanical tests are preferably performed with a sample number of 6 for each particular test.

Tensile tests are preferably performed at strain rates 0.01%/s, 2.2%/s, and 50%/s as this helps to determine whether the material is strain rate dependent. It is preferred that a sample size of 18 be tested as suggested by the Food and Drug Administration (Guidance Document for the Preparation of Investigational Device Exemptions and Premarket Approval Applications for Intra-Articular Prosthetic Knee Ligament Devices, 1987).

In a preferred embodiment of the present invention, the braided construct is composed of three regions, with two end sections designated for attachment of the construct, and the middle region which serves as the replacement ligament or tendon. In this embodiment, the middle region differs from the two end-regions in size, braiding angle, porosity and mechanical strength. The length and width of the replacement construct can be customized as needed.

FIG. 1 depicts a three-dimensional braided construct 2 with two end sections 4, 6 and a middle region 8.

For ligament or tendon repair and reconstruction, the 3-D braided scaffolds are preferably seeded with cells, preferably mammalian cells, more preferably human cells. Various cell types can be used for seeding. In a preferred embodiment, for ligament and tendon replacement, the cells are either mesenchymal in origin or capable of generating mesenchymal cells. Accordingly, preferred cell types are those of the connective tissue, as well as stems cells, more preferably pluripotent stem cells. For repair or reconstruction of the ACL ligament, it may be preferable to seed the scaffold with ACL host cells. As will be understood by those of skill in the art upon reading this disclosure, however, the scaffolds of the present invention can actually be seeded with any cell type which exhibits attachment and ingrowth and is suitable for the intended purpose of the braided scaffold. Some exemplary cell types which can be seeded into these scaffolds include, but are not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells.

Cells used in the present invention are first harvested, grown and passaged in tissue cultures. The cultured cells are then seeded onto the 3-D braided scaffold to produce a graft material composed of living cells and degradable matrix. This graft material can then be surgically implanted into a patient at the site of ligament or tendon injury to promote healing and repair of the damaged ligament or tendon. Additional advantages of the braided structure include its increased ease in implantation compared to prior art constructs prepared from fiber bundles.

Design parameters such as polymer composition and the response of primary ACL cells to 3-D braided constructs were examined. Fibronectin (FN), one of the most abundant extracellular adhesion proteins found in the body, is believed to be up-regulated during ligament formation. Consequently, for these experiments constructs were pre-coated with FN to enhance initial cell adhesion. The attachment and growth of ACL cells on three types of degradable polymers with various porosities were examined Scaffold porosity ranged from 54% to 63%, with PLA constructs having a porosity of 53.5±6.9%, PGA having a porosity of 63.3±7.3%, and PLAGA constructs having an average porosity of 62.9±3.6%. Average pore diameter was similar between PLAGA and PLA (235-250 µm) constructs, but smallest for PGA (177 µm).

Primary ACL ligament-like cells exhibited semi-ovoid, fibroblast-like morphology and when confluent, formed multinucleated cultures with specific growth orientations. Cell growth and morphology was dependent on polymer composition and porosity. Extensive sheets of cells were observed on all three types of polymers, but the morphology and cell spreading were different from PLAGA to PLA scaffolds. Cell spreading was found to be less on PLAGA, while the surface on both PGA and PLA were smoother and had fewer cellular bundles. Quantitative cellular growth (n=4) also revealed higher cells numbers on PLAGA and PLA, when compared to PGA. Pre-coating the construct with fibronectin resulted in an increase in proliferation, as reflected in a more rapid decrease in solution pH when compared to uncoated constructs, and controls without cells or fibronectin. It is likely that fibronectin increased the initial number of cells attached to the construct and consequently increased cellular growth and metabolism in the long-term cultures. Thus, the ACL cellular response was dependent on polymer composition and porosity. Further, pre-coating of constructs with fibronectin increased cell attachment and growth on these scaffolds.

The following nonlimiting examples are provided to further illustrate the present invention.

EXAMPLES

Example 1

Microfiber Matrices

An electrospinning technique was used to produce biodegradable non-woven fiber scaffold with an approximate thickness of 0.5 mm. In this procedure, PLAGA (50:50) was dissolved in methylene chloride to produce a 1:4 weight:volume solution. In the electrospinning process, a 20 kV electric potential was applied to the polymer solution and a collection screen to create an electric field. The polymer solution was then sprayed onto the collection screen for 30 minutes. This resulted in a uniform non-woven microfiber matrix attached on the screen. The matrix was removed, and cut into 1 cm$^2$ pieces.

Example 2

3-Dimensional Fiber Braid

Three-dimensional fibrous matrices were fabricated using a 3-D braiding process as described by Ko, F. K. in Textile Structural Composites, eds. Chou, T. W. and Ko., F. K. (Elsevier, Amsterdam, 1989). In this procedure, PLAGA fiber (5:95 PLAGA) was laced to produce yarns with a fiber density of 30 and 60 fibers per yarn. Yarns were then placed in a custom built braiding loom with a 6 by 12 carrier arrangement. Sequential motion of the carriers [alternating rows and columns] resulted in the formation of two rectangular 3-D braids: a 30 yarn braid [braid #1] and a 60 yarn braid [braid #2].

Example 3

In Vitro Cell Culture

Matrices were evaluated in a 2-week cell culture study using fibroblasts and primary culture osteoblasts. All matrices were UV sterilized for 24 hours per side prior to cell culture. Primary culture osteoblasts isolated from neonatal rat calvaria were grown to confluence in Ham's F-12 medium (GIBCO), supplemented with 12% fetal bovine serum [FBS] (Sigma), as described by Jarcho, M. *Clin. Ortho.* 1981 157:259. Mouse fibroblast cells (BALB/C C7 purchased from ATCC: Arlington Va.) were grown to confluence in DMEM supplemented with 10% FBS. Cells were seeded onto UV sterilized matrices at a density of 5×10$^5$ cells/matrix. Cells were cultured on the matrices for 1, 3, 7, 10, and 14 days, and were maintained with DMEM (10% FBS). At the various time points, cells were fixed in glutaraldehyde, and dehydrated through a series of ethanol dilutions. Samples for scanning electron microscopy [SEM] were sputter coated with gold (Denton Desk-1 Sputter Coater). Matrix and cellular structure was visualized by SEM (Amray 3000) at an accelerating voltage of 20 kV.

Example 4

Degradation Properties of Various Polymers

Multifilament fibers of L-poly-lactide (PLA, 70 denier), poly-glycolide (PGA, 60 denier) and their 82:18 co-polymer (PLAGA, 70 denier) were laced into 10 multi-fiber bundles for use in degradation studies. The bundles were cut to a length of 6 cm and sterilized with 70% alcohol followed by UV irradiation. The polymer bundles were soaked in 10 ml of phosphate buffered saline (PBS, pH=7.3), and in 10 ml of cell culture medium (αMEM, pH=7.3) supplemented with 10% Fetal Bovine Serum, L-glutamine and 1% antibiotics. The samples were shaken and maintained at 37° C. in a water bath for up to 3 weeks. The immersion ratios for both solutions were as follows, PLA at 0.6 mg/ml, PLAGA at 0.8 mg/ml and PGA at 0.7 mg/ml. The solutions were changed weekly, and at 1, 2, 3 and 4 weeks, pH (n=8) was measured and the amount of monomer in solution were quantified by high performance liquid chromatography (HPLC).

At 2 and 4 weeks after immersion, molecular weight, mass retention and mechanical properties of the bundles (n=5) were determined. Degradation-related morphological changes were examined using scanning electron microscopy. For mass retention measurements, the bundles were rinsed and lyophilized for 24 hours. The dry weight was recorded (n=4) and the same samples were used for molecular weight (MW) determination. Molecular weights (n=3) for PLA and PLAGA (82:18) were measured by gel permeation chromatography in tetrahydrofuran, using polystyrene standards. The mechanical properties of the yarn under tension were tested on a Instron machine (Model 4442, Instron Inc., Mass.), using a 500 N load cell (gauge length=3 cm), at a strain rate of 2% per second.

Example 5

Effect of Polymer Construct on Morphology and Growth of Anterior Cruciate Ligament Cells Fibrous scaffolds were fabricated using the 3-D braiding process described in Example 2. Fibers of L-polylactide (PLA, 70 deniers), polyglycolide (PGA, 60 deniers) and polylactide-co-glycolide 82:18 (PLAGA, 70 denier) were laced into 10 fiber/yarn bundles and these yarns were then braided using a 3-D circular braiding machine. Circular 3-D braids of 24 yarns were formed and cut into 1.5 cm lengths for these experiments. Dacron constructs were similarly formed and used as controls.

The porosity, pore diameter and total pore area of the construct were determined using the Autopore III porosimeter (Micromimetics). Scanning Electron Microscopy (SEM) was used to confirm pore distribution and examine pore geometry. The samples were UV sterilized prior to culture. The constructs were each coated with reconstituted human fibronectin (10 μg/ml) for 30 minutes.

Primary ACL cells were isolated from 1 kg New Zealand white rabbits. The excised ACL was digested using a 0.1% collagenase solution, and only cells collected from fourth digestion were selected for the study. Cells were cultured in αMEM+10% fetal bovine serum, L-glutamine and 1% antibiotics at 37°C. and 5% $CO_2$. ACL cells were seeded on the scaffolds at a density of 80,000 cells/scaffold and grown for up to 28 days. Tissue culture plastic and Dacron served as control groups. Media were exchanged every two days and for each time point, the pH was measured. Cell growth was measured using the cell-titer 96 assay. Cell morphology and growth on the scaffolds were imaged using SEM.

What is claimed is:

1. A ligament or tendon scaffold comprising:
   a three-dimensional braid prepared by a three dimensional braiding technique,
   said braid comprising biodegradable polymer fibers,
   wherein said braid terminates in three-dimensional, braided first and second attachment ends and said braid includes a three-dimensional, braided middle region that differs from both of said attachment ends in size, braiding angle, porosity, and mechanical strength to facilitate a differential cellular response in said middle region as compared with said first and second attachment ends.

2. The scaffold according to claim 1 wherein said braid has a substantially circular cross-section.

3. The scaffold according to claim 1 wherein said braid has a substantially rectangular cross-section.

4. The scaffold according to claim 1 wherein said fibers comprise a poly(hydroxy)ester.

5. The scaffold according to claim 4 wherein said fibers comprise a polylactic acid, a polyglycolic acid, or a copolymer of a polylactic acid and a polyglycolic acid.

6. The scaffold according to claim 1 wherein said fibers comprise at least one lactic acid polymer.

7. The scaffold according to claim 6 wherein said fibers comprise poly-L-lactic acid.

8. The scaffold according to claim 1 wherein braid is formed from a plurality of bundles comprising about 10 to about 60 fibers per bundle.

9. The scaffold according to claim 1 wherein said braid has an average porosity of about 54% to about 63%.

10. The scaffold according to claim 1 wherein said braid has an average pore diameter of about 177 μm to about 250 μm.

11. The scaffold according to claim 1 wherein said braid is formed using a three dimensional braiding technique that utilizes a row and column braider.

12. The scaffold according to claim 1 that is adapted to repair, reconstruct, or replace an anterior cruciate ligament.

13. A method comprising implanting a scaffold according to claim 1 in a patient in need thereof.

14. The method according to claim 13 comprising implanting said scaffold to repair, reconstruct, or replace an anterior cruciate ligament of said patient.

15. The scaffold according to claim 1 wherein said braid is formed using a three dimensional braiding technique that utilizes a circular braider.

16. The scaffold according to claim 1 wherein said braid has a substantially circular cross section.

17. The scaffold according to claim 1 wherein said braid has a substantially rectangular cross section.

18. The scaffold according to claim 1 wherein said braid comprises braided bundles of multi-filament, biodegradable polymer fibers.

* * * * *